(12) United States Patent
Tao et al.

(10) Patent No.: US 8,795,576 B2
(45) Date of Patent: Aug. 5, 2014

(54) RADIOPAQUE CANNULA MARKER

(75) Inventors: Zhenghong Tao, Winchester, MA (US);
Stephen Vaughan, Medford, MA (US);
Marie-Eve Mongeau, Newbury, MA (US)

(73) Assignee: Abiomed, Inc., Danvers, MA (US)

( * ) Notice: Subject to any disclaimer, the term of this patent is extended or adjusted under 35 U.S.C. 154(b) by 0 days.

(21) Appl. No.: 13/307,998

(22) Filed: Nov. 30, 2011

(65) Prior Publication Data

US 2012/0142995 A1 Jun. 7, 2012

Related U.S. Application Data

(60) Provisional application No. 61/418,743, filed on Dec. 1, 2010.

(51) Int. Cl.
*B27N 7/00* (2006.01)

(52) U.S. Cl.
USPC .......................................... 264/340; 606/108

(58) Field of Classification Search
USPC ................... 606/108; 600/16; 264/340, 405
See application file for complete search history.

(56) References Cited

U.S. PATENT DOCUMENTS

| 6,210,396 | B1 * | 4/2001 | MacDonald et al. ......... 604/529 |
| 6,520,934 | B1 | 2/2003 | Lee et al. |
| 6,974,436 | B1 | 12/2005 | Aboul-Hosn et al. |
| 2005/0065434 | A1 * | 3/2005 | Bavaro et al. ................. 600/424 |
| 2005/0149060 | A1 * | 7/2005 | Thorstenson et al. ........ 606/108 |
| 2007/0197856 | A1 * | 8/2007 | Gellman et al. ................ 600/16 |
| 2008/0243227 | A1 * | 10/2008 | Lorenzo ....................... 623/1.15 |
| 2009/0171367 | A1 * | 7/2009 | Hardin, Jr. .................... 606/108 |

FOREIGN PATENT DOCUMENTS

| EP | 1 847 288 | 10/2007 |
| WO | WO-2007/124161 | 11/2007 |

OTHER PUBLICATIONS

International Preliminary Report on Patentability for PCT Appl. Serial No. PCT/US2011/062664 mailed Jun. 13, 2013 (7 pages).

* cited by examiner

*Primary Examiner* — Christopher D Koharski
*Assistant Examiner* — Michael Carey
(74) *Attorney, Agent, or Firm* — Foley & Lardner LLP; Aaron W. Moore; Moses A. Heyward

(57) ABSTRACT

A method is disclosed of applying a radiopaque marker to a cannula for use with an intracardiac pump, the method including: obtaining a band of radiopaque polymer material; placing the band around an outer diameter of the cannula, the cannula including a flexible tubular wall formed around and supported by a coil of shape memory material; placing a heat shrink tube around the band and the cannula; heating the band and the polymer tube to: soften the band, cause the heat shrink tube to shrink and apply force on the softened band towards the cannula, and cause the softened band to be welded to the cannula to form a radiopaque marker in a portion of the tubular wall; and removing the heat shrink tube.

19 Claims, 15 Drawing Sheets

RADIOPAQUE CANNULA MARKER

CROSS REFERENCE TO RELATED APPLICATIONS

This application claims benefit of U.S. Provisional Application No. 61/418,743 filed Dec. 1, 2010, the entire contents of which are incorporated by reference herein.

BACKGROUND

An intracardiac blood pump is a blood pump that is at least partially introduced into the heart to deliver blood from the heart into an artery, wherein the pump may protrude through a surgical opening in the heart. Typical intracardiac blood pumps have a maximum outer diameter of about 10-15 mm. A special form of intracardiac blood pumps are intravascular blood pumps. They are introduced into the heart through the vascular system of the patient, the incision site being spaced from the heart. Typically, intracardiac blood pumps inserted percutaneously into a patient's body are highly miniaturized, with a maximum outer diameter of 8 mm or less.

Examples of intracardiac and intravascular blood pumps may be found in the following references, the entire contents of each of which is incorporated by reference herein: International Publication WO/2005/016416, published Apr. 20, 2006, International Publication WO/2005/016416, published Feb. 24, 2005; International Publication WO/2002/043791, published Jun. 6, 2002; International Publication WO/2002/015963, published Feb. 28, 2002; International Publication WO/2001/039817, published Jun. 7, 2001; and International Publication WO/1999/058170 published Nov. 18, 1999.

Further examples include the family blood pumps available from Abiomed, Inc. of Danvers, Mass. under the Impella brand, including the Impella 2.5 pump, the Impella 5.0 pump, and the Impella LD.

SUMMARY

In many applications, medical imaging techniques including X-ray imaging, fluoroscopy, etc. are used by practitioners to guide the insertion and positioning of intracardiac and intravascular blood pumps or other devices. In such applications it would be advantageous to improve the visibility of the pump devices. In particular, some pumps include a cannula or other portion made of a material that has a low radiopacity, and therefore low visibility to X-ray or fluoroscopic imaging. However accurate positioning of these low radiopacity portions may be important to the proper function of the device. In such cases, it would be advantageous to provide a radiopaque marker on the cannula (or other low radiopacity portion) to improve visibility.

The applicants have realized that the techniques described herein may be used to provide a radiopaque marker on a medical device. In some embodiments, the radiopaque marker may be applied to a cannula used in the medical device. In some embodiments, the cannula is included in a device such as an intracardiac or intravascular blood pump.

Advantageously, in some embodiments, the radiopaque marker may by applied to the cannula without adversely impacting the size, strength, flexibility, and shape of the cannula. For example, in some embodiments, the marker is provided without substantially increasing the outer diameter of the cannula. This may be particularly advantageous when implanting the cannula with an introducer device that can only be used to introduce objects with a limited outer diameter.

In some embodiments, the marker is provided while maintaining a smooth cannula surface that is free or substantially free of sharp edges, roughness, or other features that would promote haemolysis, thrombus and potential damage to the subject, at the implantation site, or other unwanted effects.

In one aspect, a method is disclosed of applying a radiopaque marker to a cannula for use with an intracardiac pump, the method including: obtaining a band of radiopaque polymer material; placing the band around an outer diameter of the cannula, the cannula including a flexible tubular wall formed around and supported by a coil of shape memory material; placing a heat shrink tube around the band and the cannula; heating the band and the polymer tube to: soften the band, cause the heat shrink tube to shrink and apply force on the softened band towards the cannula, and cause the softened band to be welded to the cannula to form a radiopaque marker in a portion of the tubular wall; and removing the heat shrink tube.

In some embodiments, after removing the heat shrink tube, the portion of the tubular wall including the radiopaque marker has a substantially smooth outer surface.

In some embodiments, the outer diameter of the portion of the tubular wall including the radiopaque marker varies from the outer diameter of an adjacent portion not including the radiopaque marker by less than 0.1%.

In some embodiments, the outer diameter of the portion of the tubular wall including the radiopaque marker varies from the outer diameter of an adjacent portion not including the radiopaque marker by less than 0.01%.

In some embodiments, the outer diameter of the portion of the tubular wall including the radiopaque marker is substantially the same as the outer diameter of an adjacent portion not including the radiopaque marker.

In some embodiments, the portion of the tubular wall including the radiopaque marker has a substantially smooth outer surface that is substantially free of surface variations that would promote haemolysis or thrombus during use.

In some embodiments, the radiopaque band includes a mixture of a radiopaque material with a non-radiopaque polymer, and where the mixture includes at least 80% of the radiopaque material by weight.

Some embodiments include forming the radiopaque band, where forming the radiopaque band includes: mixing the radiopaque material with the non-radiopaque polymer to form the mixture; forming a radiopaque tube by extruding the mixture; cutting the radiopaque tube to form at least one band.

In another aspect, a method of applying a radiopaque marker to a cannula for use with an intracardiac pump is disclosed, the method including: obtaining a radiopaque metallic element; placing the marker in contact with an outer diameter of the cannula, the cannula including a flexible tubular polymer wall supported by a coil of shape memory material; placing a sleeve of a non-metallic material surrounding the a radiopaque metallic element and the cannula; placing a heat shrink tube surrounding sleeve; heating the sleeve and the heat shrink tube to soften the sleeve, cause the heat shrink tube to shrink and apply force on the softened band towards the cannula, and cause the softened band to be welded to the cannula around the element to form a radiopaque marker in a portion of the tubular wall; and removing the heat shrink tube.

In some embodiments, after removing the heat shrink tube, the portion of the tubular wall including the radiopaque marker has a substantially smooth outer surface of non-metallic material which surrounds the element.

In some embodiments, the outer diameter of the portion of the tubular wall including the radiopaque marker varies from the outer diameter of an adjacent portion not including the radiopaque marker by less than 1.0%.

In some embodiments, the outer diameter of the portion of the tubular including the radiopaque marker varies from the outer diameter of an adjacent portion not including the radiopaque marker by less than 0.1%.

In some embodiments, the element is completely covered by the smooth outer layer, such that no surfaces or edges of the marker are exposed.

In some embodiments, the smooth outer layer is substantially free of variations in outside diameter corresponding to the covered marker.

In some embodiments, the smooth outer layer is substantially free of surface variations that would promote haemolysis or thrombus during use.

In some embodiments, the element includes an elastic member, and placing the element in contact with an outer diameter of the cannula includes using an elastic force from the elastic member to clamp the element to the cannula.

In some embodiments, the element includes a C-shaped partial ring.

In some embodiments, the smooth outer prevents the element from moving along a length of the cannula.

In another aspect, a cannula having a radiopaque marker for use with an intracardiac pump is disclosed. In some embodiments, the cannula is produces using any of the methods described above.

Various embodiments may include any of the above described features, either alone, or in any suitable combination.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The accompanying drawings, which are incorporated in and constitute a part of this specification, illustrate one or more embodiments described herein and, together with the description, explain these embodiments. Like reference characters refer to the same parts throughout the different views. The drawings are not necessarily to scale, emphasis instead being placed upon illustrating the principles of the embodiments.

DETAILED DESCRIPTION

Figure 1:
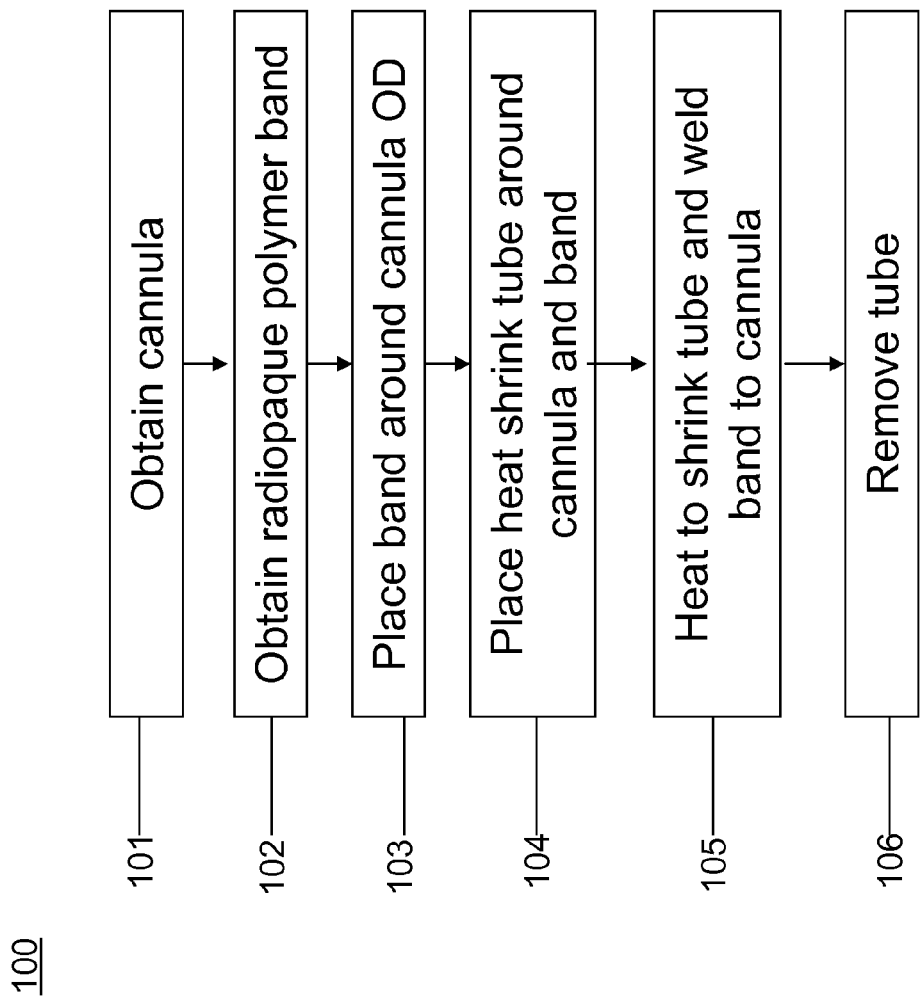
FIG. 1 is a flow diagram showing a method of applying a radiopaque marker to a cannula.

Referring to FIG. 1, a method 100 is disclosed for applying a radiopaque marker to cannula used in a medical device, such as an intracardiac pump. FIGS. 2A-2E illustrate the method steps for an exemplary embodiment. Each of FIGS. 2A-2E show a cross section of the cannula corresponding to a plane the slices through the cannula and includes a central axis of the cannula running from an inflow end at the left side of the figure to an outflow end at the right side of the figure.

Figure 2A:
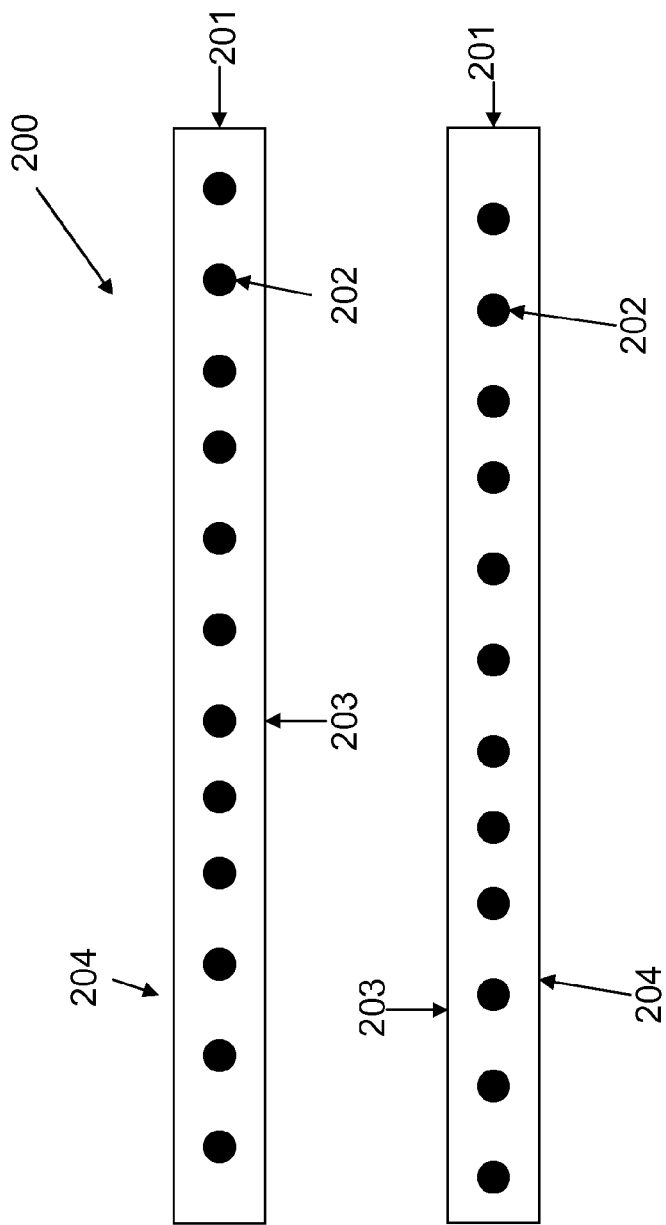
FIGS. 2A-2E illustrate the method of applying a radiopaque marker to a cannula shown in FIG. 1. Each of FIGS. 2A-2E show a cross section of the cannula at various steps in the method.

In step 101 a cannula is obtained. FIG. 2A shows an example of a cannula 200. The cannula 200 includes a tubular wall 201 reinforced by a shape memory structure 202 (as shown, a nitinol coil). The tubular wall is flexible, and may be formed of a polymer material, such as polyurethane (PU). In some embodiments, the cannula 200 advantageously provides a high degree of strength, flexibility and shape memory properties.

In some embodiments, the cannula 200 may be formed using a controlled solution casting process, resulting in a well controlled inner diameter (ID) and outer diameter (OD) of the cannula 200 For example, in some embodiments, the inner surface 203 and outer surface 204 of the tubular wall 201 may be very smooth. For example, the surfaces may be substantially free of any variations, features, rough portions, etc. that could promote haemolysis or thrombus during use of the cannula in an implantation procedure.

In step 102, a radiopaque polymer band 205 is obtained. As described below in greater detail below, the band may be formed of a mixture of non-radiopaque or only weakly radiopaque polymer material (e.g., PU) and a radiopaque material (e.g., tungsten).

Figure 2B:
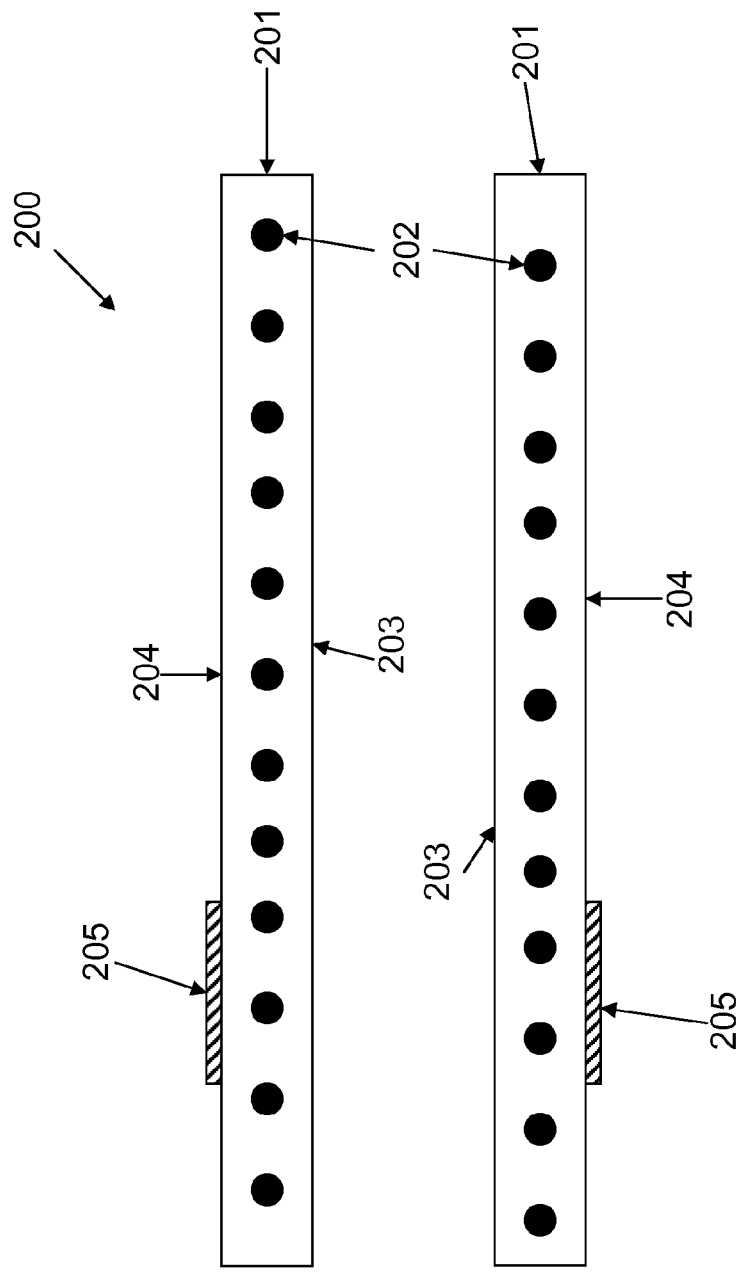

In step 103, as shown in FIG. 2B the band 205 is placed around the outer surface 204 of the cannula 200. In some embodiments, the band 205 may be thin along the direction normal to the outer surface 203 of the cannula 200. For example, the thickness of the band along this direction may be less than 1%, less than 0.1%, less than 0.001%, of the OD of the cannula 200 (e.g., in the range of 0.001% to 1.0% of the OD, or any subrange thereof).

As detailed below, in some such embodiments, the band may be made of non-radiopaque or only weakly radiopaque polymer material heavily loaded with radiopaque material, in order to ensure that the band is radiopaque despite its thinness.

Figure 2C:
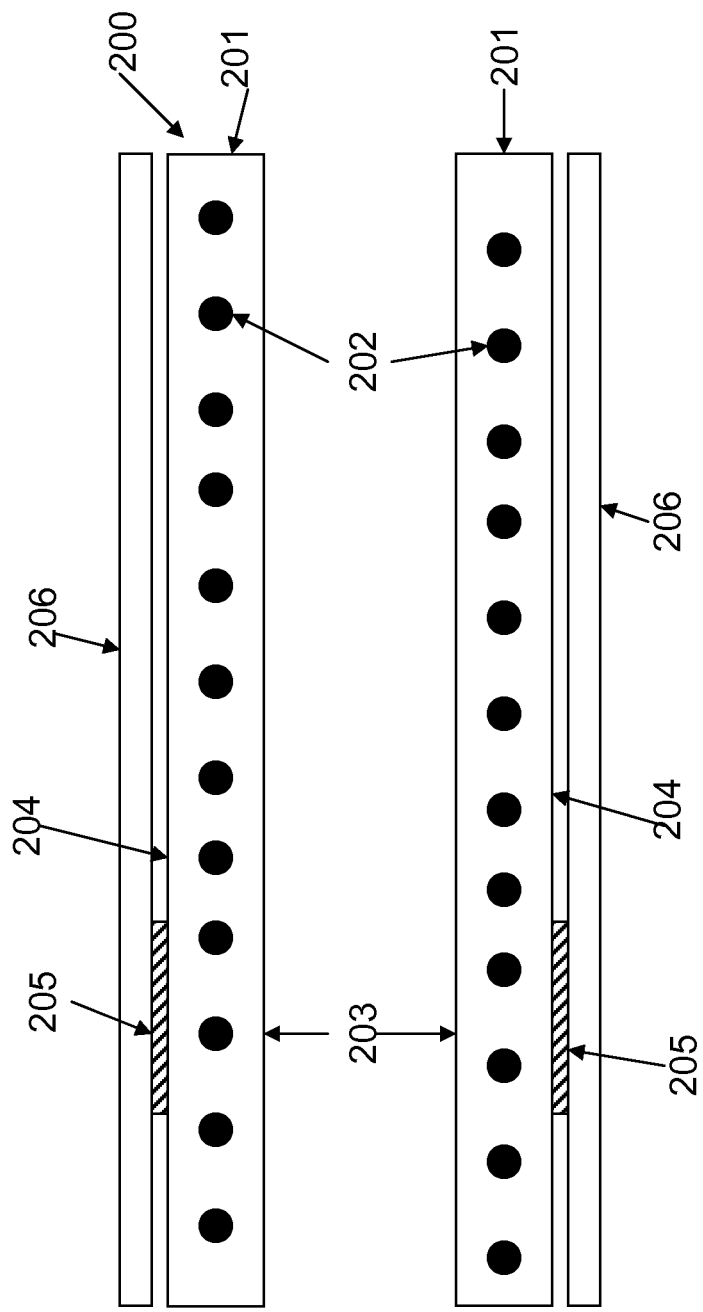

In step 104, as shown in FIG. 2C, a tube 206 of heat shrink material is placed around both the band 205 and the cannula 200. The heat shrink tube 206 may be made of any suitable heat shrink material know in the art, including, for example, fluorinated ethylene-propylene (FEP) or polytetrafluoroethylene (PTFE).

Figure 2D:
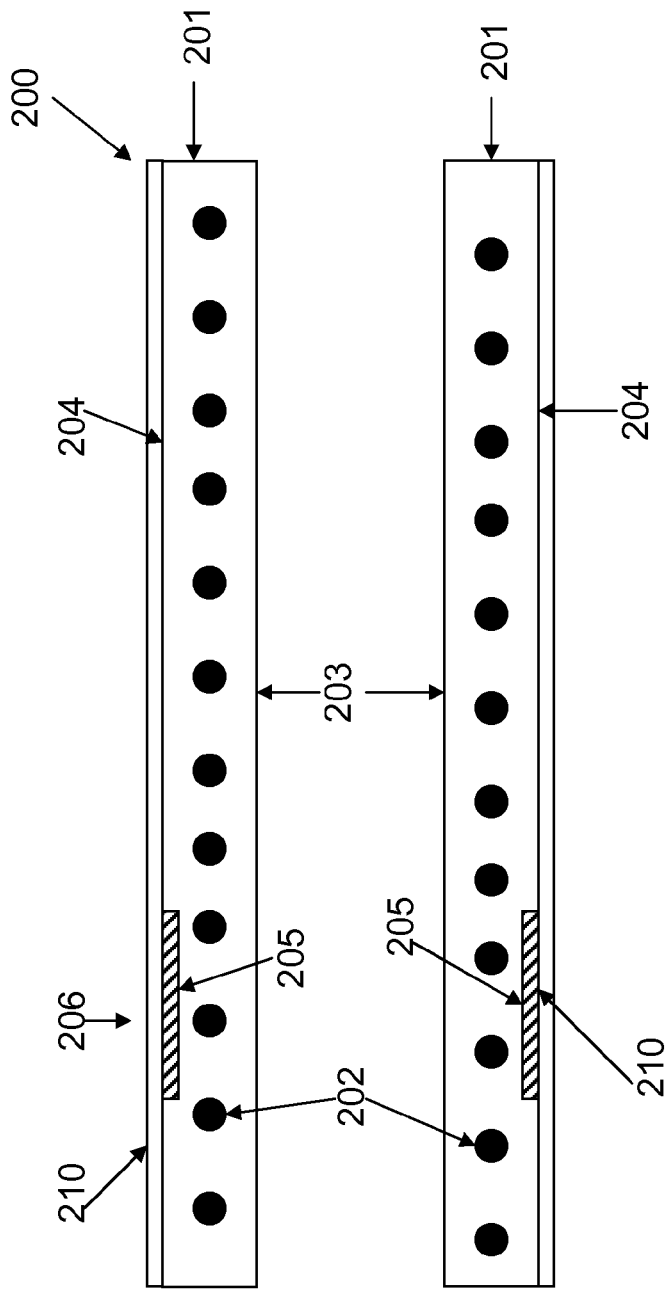

In step 105, heat is applied to the heat shrink tube 206 and the band 205, e.g., by placing the structure shown in FIG. 2C in an oven. The band 205 is heated to a temperature above its softening point. The heat shrink tube 206 shrinks in response to the heat, applying a force on the softened band 205 in the direction towards the cannula 200. The softened band is thereby welded onto the outer surface 204 of the cannula 200, to form a radiopaque marker 210 as shown in FIG. 2D.

Figure 2E:
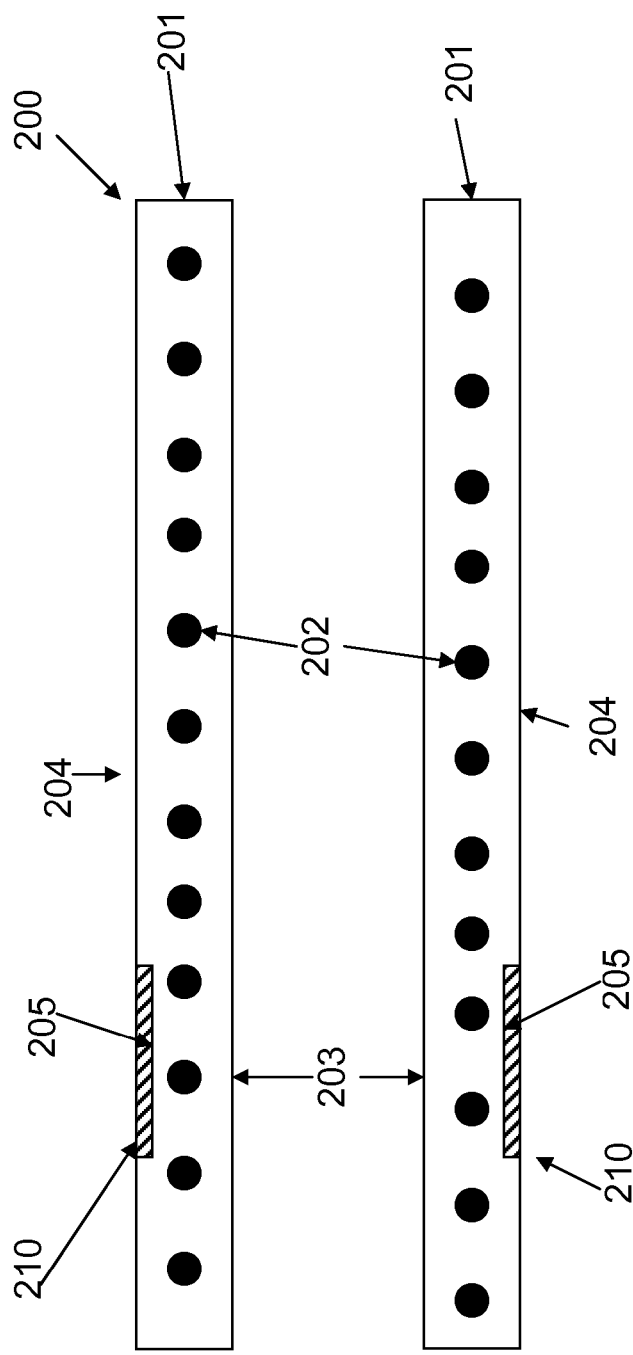

In step 106, after the cannula 200 is allowed to cool, the heat shrink tube 206 is removed, exposing the outer surface 204 of the cannula 200, as shown in FIG. 2E. In some embodiments, the heat shrink tube 206 acts as a mold, ensuring that the portion of the outer surface 204 of the cannula 200 that includes the marker 210 is substantially smooth. In some embodiments, this smooth surface is substantially free of any variations, features, rough portions, etc. that could promote haemolysis or thrombus during use of the cannula in an implantation procedure.

In some embodiments, e.g., as shown in FIG. 2E, the outer diameter of the cannula at portion of the outer surface 204 that includes the marker 210 is the same as or substantially the substantially the same as the adjacent portions that do not include the marker 210. In other words, the use of the heat shrink tubing 206 may ensure that the marker 210 is formed flush with the outer surface of the remainder of the cannula 200.

In some embodiments, during the heating, the cannula 200 may be mounted on a mandrel or other support structure which maintains the ID of the cannula 200.

In other embodiments, the outer diameter of the portion of the cannula 200 including the radiopaque marker 210 varies from the outer diameter of the adjacent portion without the marker by less than 5%, 1%, 0.1%, 0.01% or less, (e.g. in the range of 0.001% to 10% or any subrange thereof.).

In various embodiments the heating temperature and time for step 105 may be chosen based on the particular materials used and the application at hand. In one example, cannula 200 may be formed as a nitinol supported PU tube. The band 205 may be formed of tungsten loaded PU (e.g., having at least 80% tungsten by weight), and the heat shrink tube may be made of FEP heat shrink tubing. In this exemplary embodiment, a suitable heating step may include baking at about 183° C. for about 3.5 minutes.

In various embodiments, after the marker 210 has been applied to the cannula 200, further processing steps may be performed. For example, in some embodiments, the cannula 200 undergoes a bending process to obtain a desired cannula shape.

Figure 3:
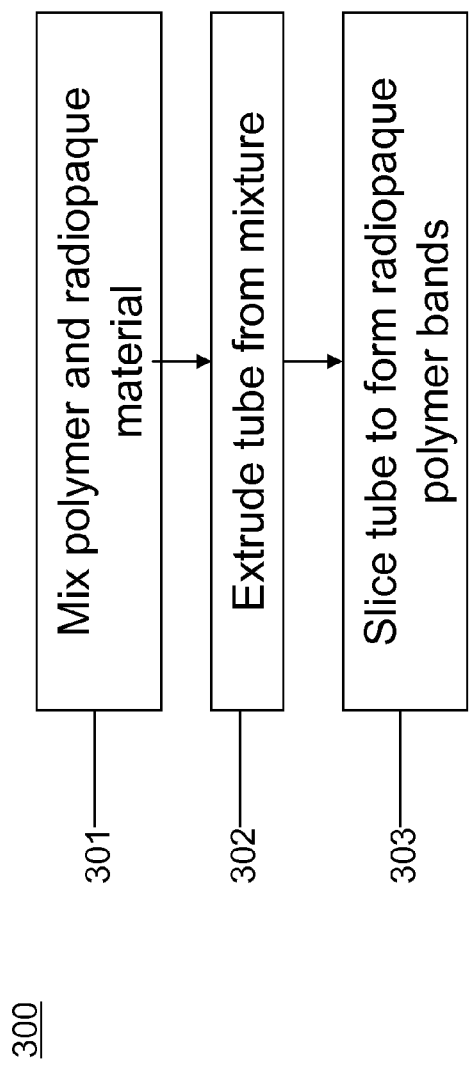
FIG. 3 is a flow diagram showing a method of making radiopaque bands.

FIG. 3 illustrates an exemplary process 300 for making a radiopaque band 205 of the type described above. In step 301, a non-radiopaque material is mixed with a radiopaque material. The non-radiopaque material may include, e.g. a plastic or polymer. In some embodiments, PU may be used. In various embodiments, the radiopaque material may include e.g. a metallic powder such as a tungsten powder. In various embodiments other radiopaque materials may be used (e.g. silver, tantalum, tin, etc.). In some embodiments, the mixing is performed using twin screw extruder device.

In step 302, the mixture is formed into a tube, e.g., using extrusion or any other suitable process known in the art. In some embodiments, extrusion is performed using twin screw extruder device.

In step 303, the tube is cut into pieces of a desired size to form the bands 205. The band may have any desired size. In some embodiments, each band 205 has a width in the range of 1 mm to 2 mm and an outer diameter of about 4 mm (e.g., corresponding the diameter of a cannula having a size of about 12 Fr on the familiar French catheter size scale).

Figure 4:
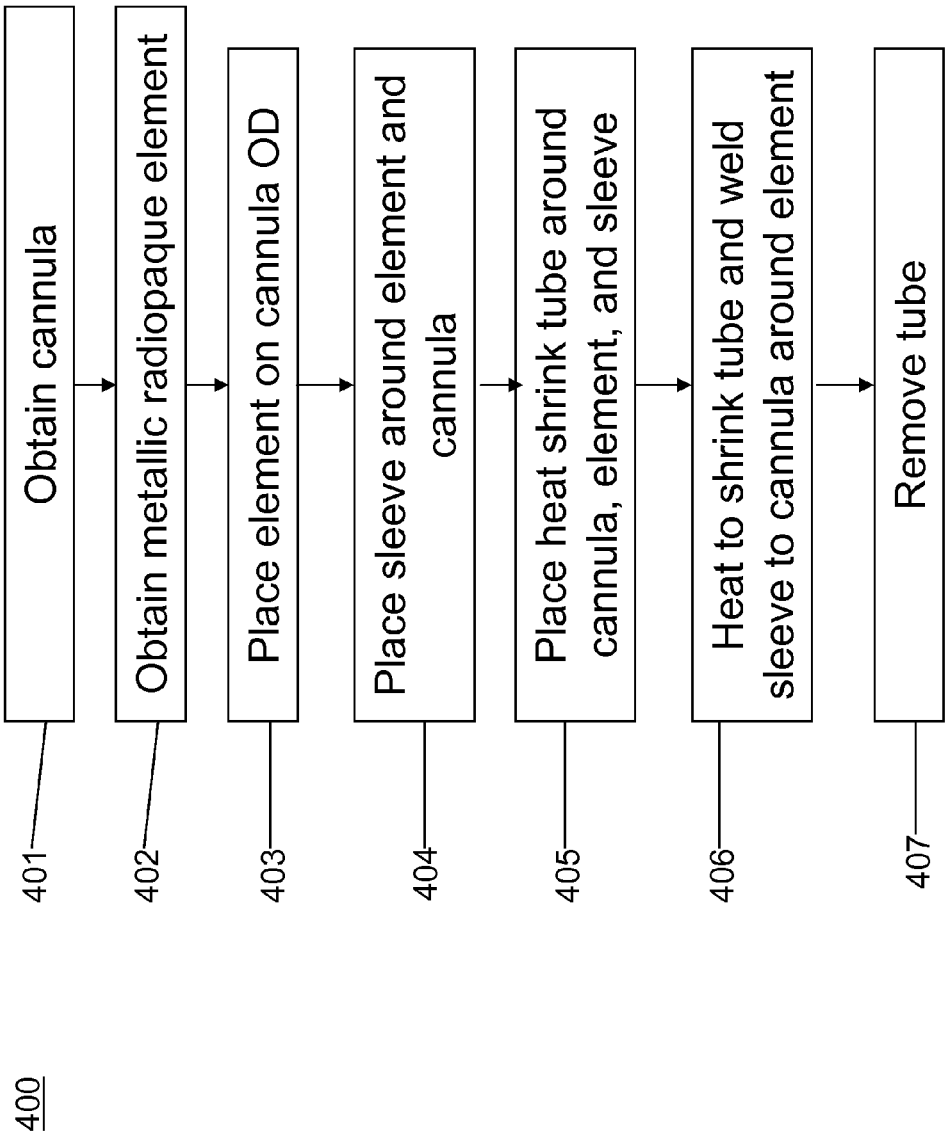
FIG. 4 is a flow diagram showing an alternative method of applying a radiopaque marker to a cannula.

Referring to FIG. 4, another method 400 is disclosed for applying a radiopaque marker to a cannula in a medical device, such as an intracardiac pump. FIGS. 5A-5D illustrate the method steps for an exemplary embodiment. Each of FIGS. 5A-5D show a cross section of the cannula corresponding to a plane the slices through the cannula and includes a central axis of the cannula running from an inflow end at the left side of the figure to an outflow end at the right side of the figure.

Figure 5A:
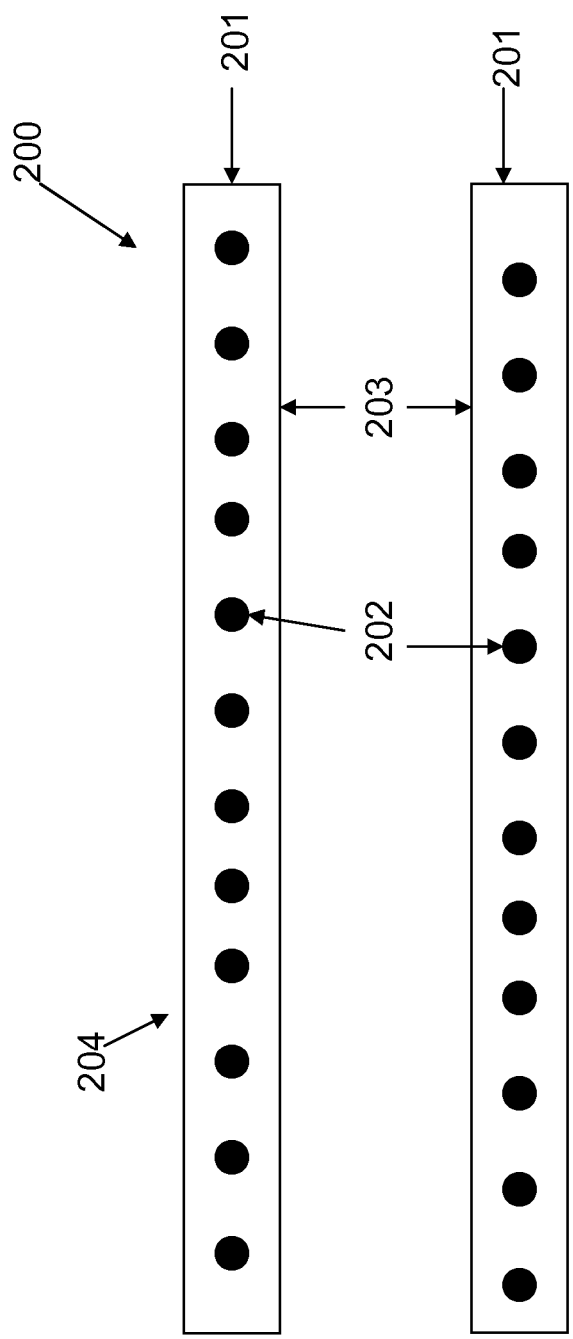
FIGS. 5A-5D illustrate the method of applying a radiopaque marker to a cannula shown in FIG. 4. Each of FIGS. 5A-5D show a cross section of the cannula at various steps in the method.

In step 401, a cannula 200 is obtained, as shown in FIG. 5A. The cannula 200 may be of the type described above with reference to FIGS. 1 and 2A-2E.

In step 402, a radiopaque element 505 is obtained. In some embodiments, the element 505 is a metallic element, e.g., made of tungsten, silver, tantalum, tin or any other suitable material.

Figure 5B:
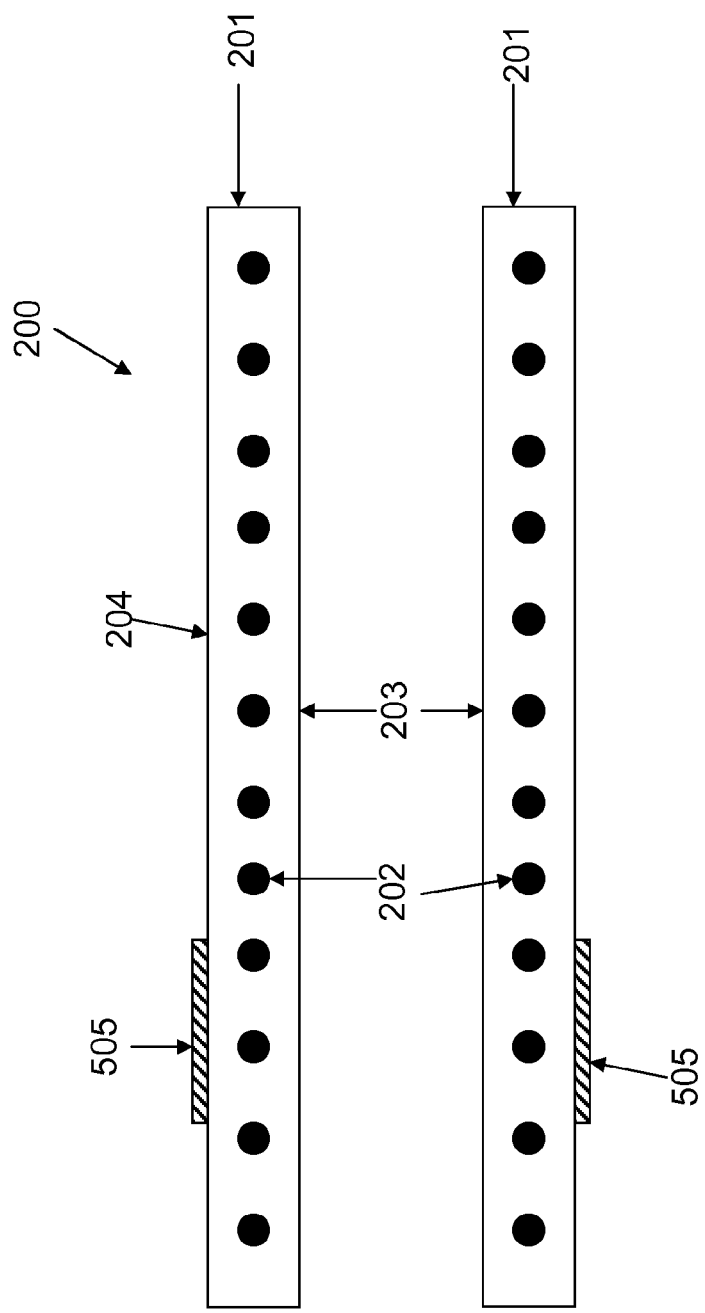
Figure 5C:
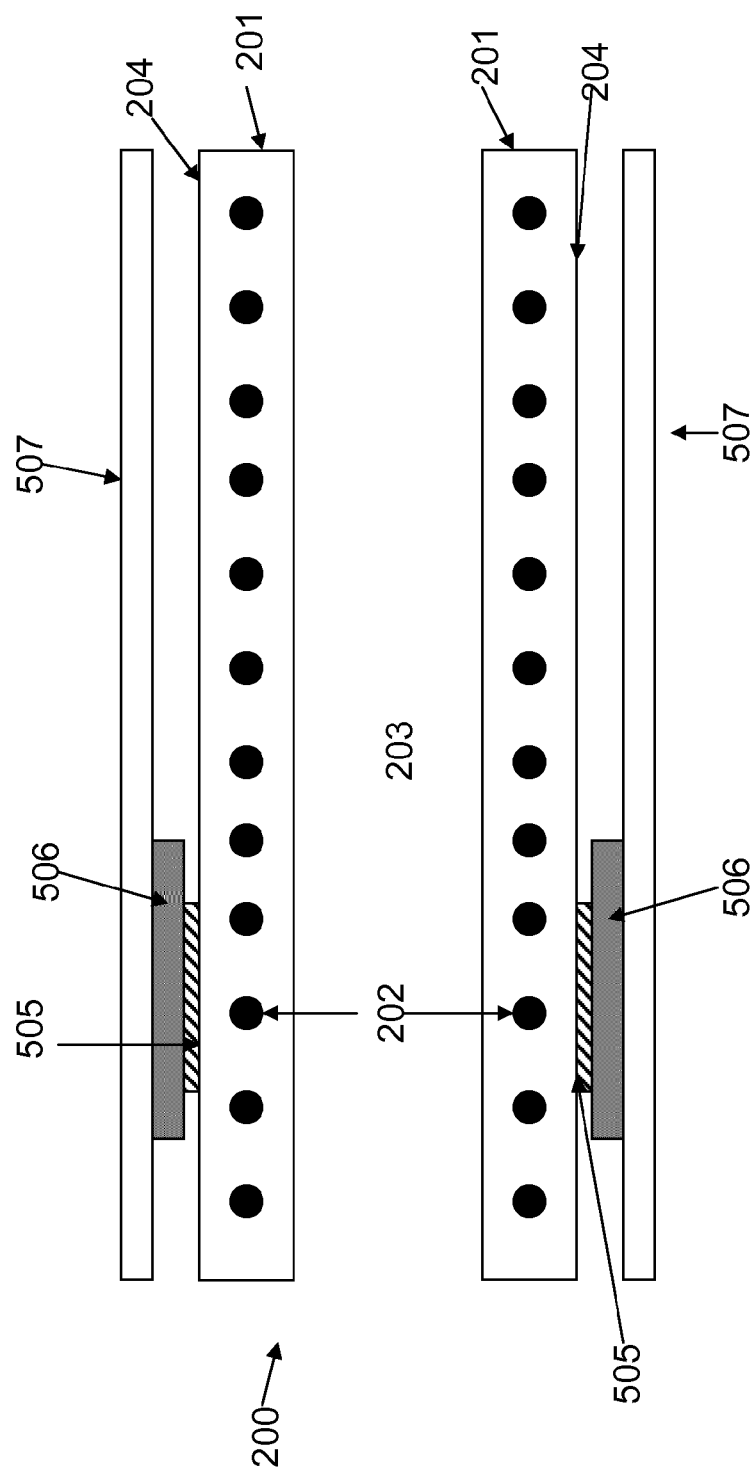

In step 403, as shown in FIG. 5B, the radiopaque element 505 is placed on the outer surface 204 of the cannula 200. For example, in some embodiments, the element 505 may be a C-shaped elastic metallic ring (i.e., a ring with a gap) that clamps on to the cannula 200 (e.g., similar to a familiar C-clamp). In various embodiments, other suitable shapes may be used for element 505.

In step 404, as shown in FIG. 5B, a sleeve 506 is placed over the radiopaque element 505 on the cannula 200. The sleeve 506 may, for example, be made of a plastic or polymer or other material. In some embodiments, the sleeve 506 is made of a non-radiopaque or weakly radiopaque material.

Figure 5D:
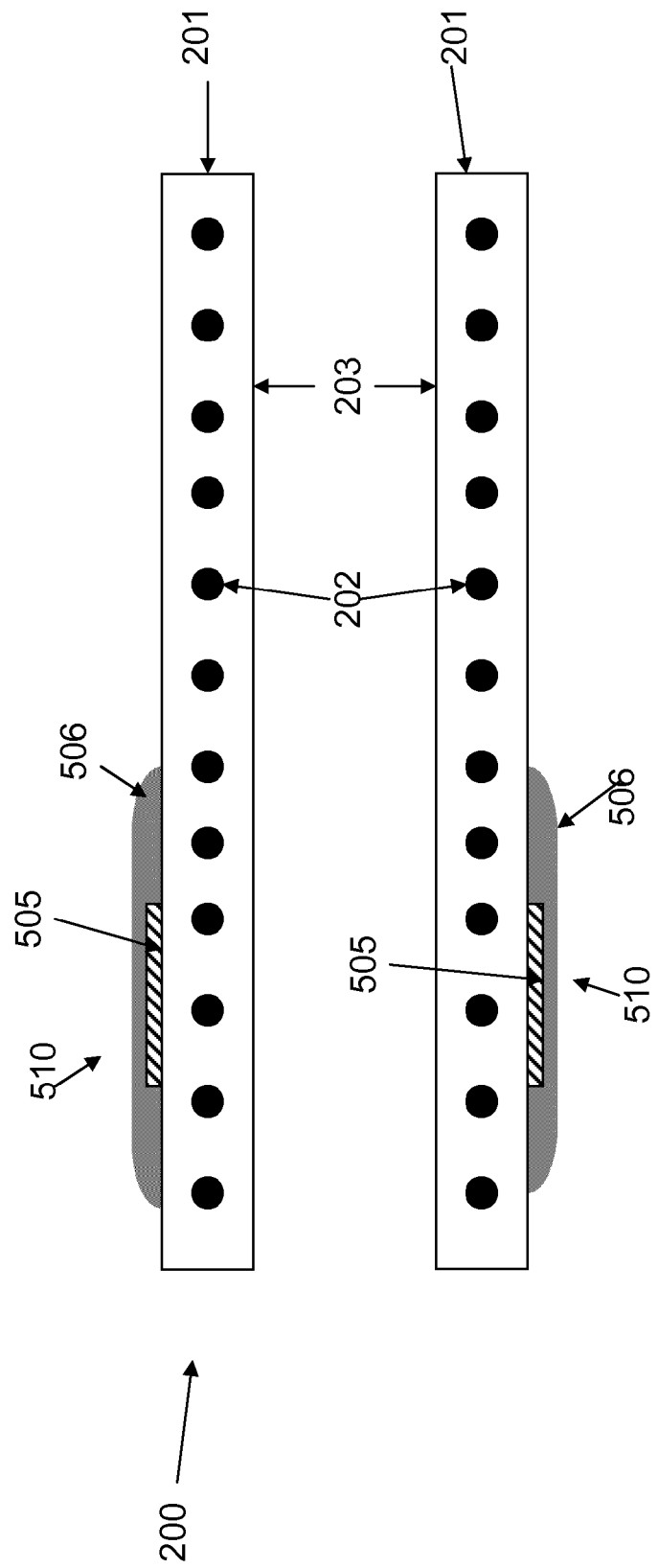

In step 405, as shown in FIG. 5D a heat shrink tube 507 is place over the sleeve 506 and radiopaque element 505 on the cannula 200. The heat shrink tube 507 may be made of any suitable heat shrink material know in the art, including, for example, fluorinated etheleyne-propylene (FEP) or polytetrafluoroethylene (PTFE).

In step 406, heat is applied to the heat shrink tube 507 and the sleeve 506, e.g., by placing the structure shown in FIG. 5D in an oven. The sleeve 506 is heated to a temperature above its softening point. The heat shrink tube 507 shrinks in response to the heat, applying a force on the softened sheath 507 in the direction towards the cannula 200. The softened sleeve 506 is thereby welded onto the outer surface 204 of the cannula 200, while forming around the radiopaque element 505. The radiopaque element is thereby attached to the cannula 200 to form a radiopaque marker 510. In some embodiments, once welded to the cannula 200, the sleeve 506 completely covers the element 505, e.g., so that no surfaces or edges of the element are exposed.

In step 407, after the cannula 200 is allowed to cool, the heat shrink tube 507 is removed, exposing the outer surface 204 of the cannula 200, as shown in FIG. 5E. In some embodiments, during step 406, the heat shrink tube 507 acts as a mold, so that the portion of the outer surface 204 of the cannula 200 overlaying the element 505 is smooth. In some embodiments, this smooth surface is substantially free of any variations, features, rough portions, etc. that could promote haemolysis or thrombus during use of the cannula in an implantation procedure.

In some embodiments (not shown), the outer diameter of the cannula at portion of the outer surface 204 that includes the marker 510 is the same as or substantially the substantially the same as the adjacent portions that do not include the marker 210. In other words, the use of the heat shrink tubing 507 may cause the element 505 to be embedded in the cannula 200 such that the marker 210 is formed flush with the outer surface of the remainder of the cannula 200.

In some embodiments, e.g., as shown in FIG. 5D the radiopaque element 550 is not fully embedded in the cannula 200. However, the welded sleeve 506 forms a smooth covering over the element 505, such that no sharp edges are exposed.

In some embodiments, the outer diameter of the portion of the cannula 200 including the radiopaque marker 510 varies from the outer diameter of the adjacent portion without the marker by less than 5%, 1%, 0.1%, 0.01% or less, (e.g. in the range of 0.001% to 10% or any subrange thereof.).

In some embodiments, during the heating, the cannula 200 may be mounted on a mandrel or other support structure which maintains the ID of the cannula.

In various embodiments, after the marker 510 has been applied to the cannula 200, further processing steps may be performed. For example, in some embodiments, the cannula 200 undergoes a bending process to obtain a desired cannula shape.

It is to be understood that, in various embodiments, a cannula with a radiopaque marker of the type described herein my be used in any of a wide variety of medical devices, including intracardiac blood pumps. As described above, in some embodiments the cannula may advantageously have a small outer diameter, and a smooth surface, suitable for use in intravascular blood pumps. In various embodiments, the cannula may be incorporated in devices of the types described in any of the references found in the background section above.

Figure 6:
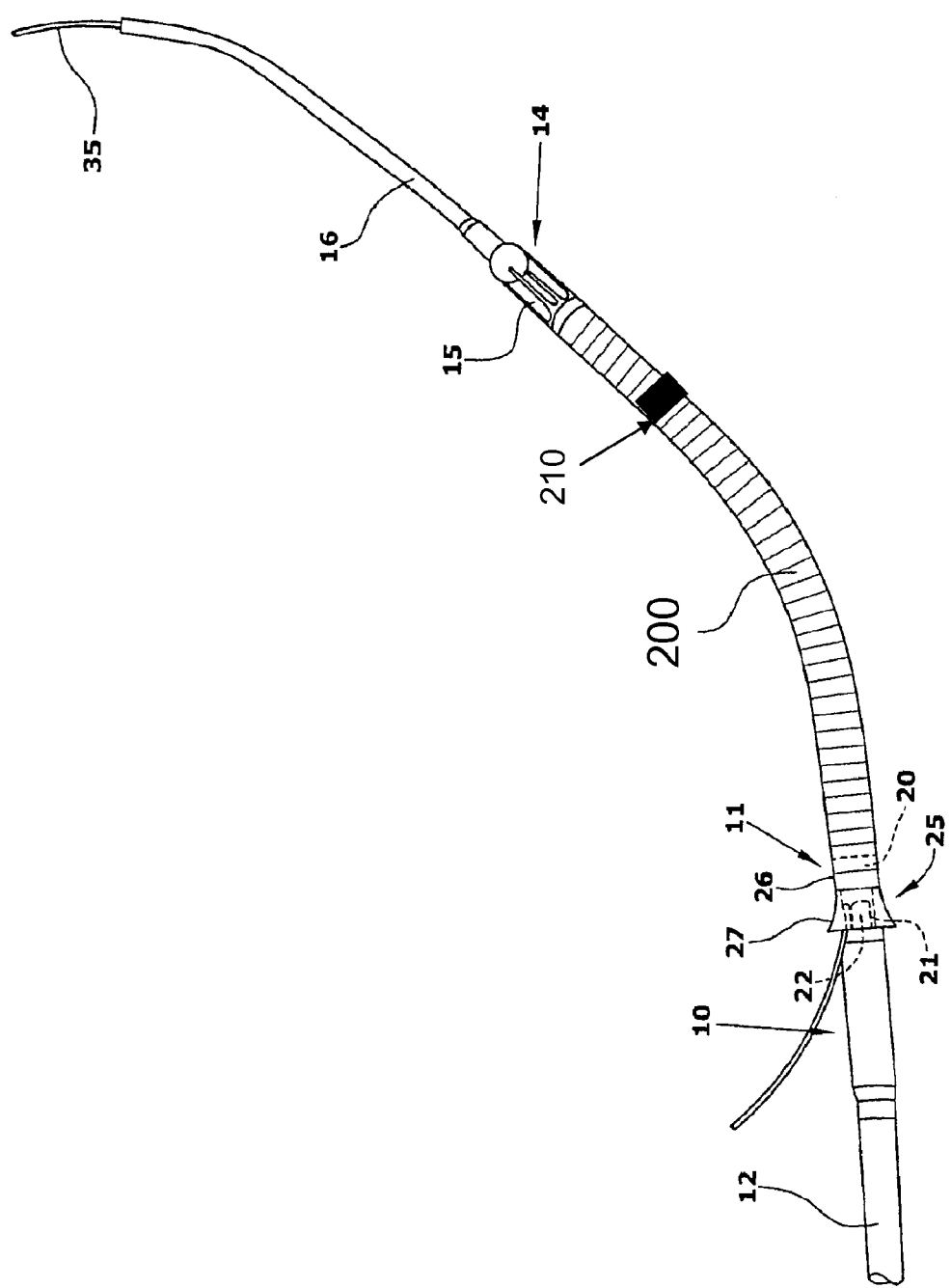
FIG. 6 is an illustration of an intracardiac blood pump featuring a cannula with a radiopaque marker.

For example, FIG. 6 illustrates the uses of a cannula 200 including a radiopaque marker 210 of the type described above in an intracranial pump device. The pump device may is of the type described in U.S. Pat. Pub. No. 2008/0086027 published Apr. 10, 2008, the entire contents of which are incorporated by reference herein.

The intracardiac pump device includes a drive portion 10 and a pump portion 11 coaxial thereto. The drive portion 10 includes a motor (not illustrated). The proximal end of the drive portion 10 is connected with a catheter 12 holding the electric lines for operating and controlling the blood pump. The pump portion 11 is connected with a cannula 200 in the form of an elongate flexible hose whose distal end is provided with a suction head 14 having inflow openings 15. Contiguous to the suction head 14 is a soft elastic extension 16 that mechanically, yet not hydraulically extends the cannula 200. This extension 16 is provided with a pigtail tip to allow for atraumatic support on body tissue.

The pump portion 11 has a pump ring 20 that is connected with the drive portion 10 through longitudinally extending webs 21. Between the webs 21, the discharge ports 22 are situated through which blood exits radially to then flow along the outer side of the drive portion 10. In some embodiments, a screen 25 is provided at the pump portion 11. It includes an annular sleeve 26 sitting on the pump ring 20 and a continuously flaring guide portion 27 projecting proximally from the pump ring. The beginning of the guide portion 27 is at the upstream end of the discharge ports 22, i.e. at the end adjoining the pump ring 20.

In some embodiments, the outer diameter of the drive portion 10 and of the pump portion 11 is 4.0 mm. The outer diameter of the screen 25 is 5.6 to 6.0 mm. The wall thickness of the screen is 0.1 to 0.2 mm. The screen is made of a flexible material, for example of polyurethane. It may be formed integral with the cannula 200. As shown, a guide wire 35 has been inserted through the device for use in positioning the device in a subject (e.g., using the techniques described below with reference to FIG. 7).

Figure 7:
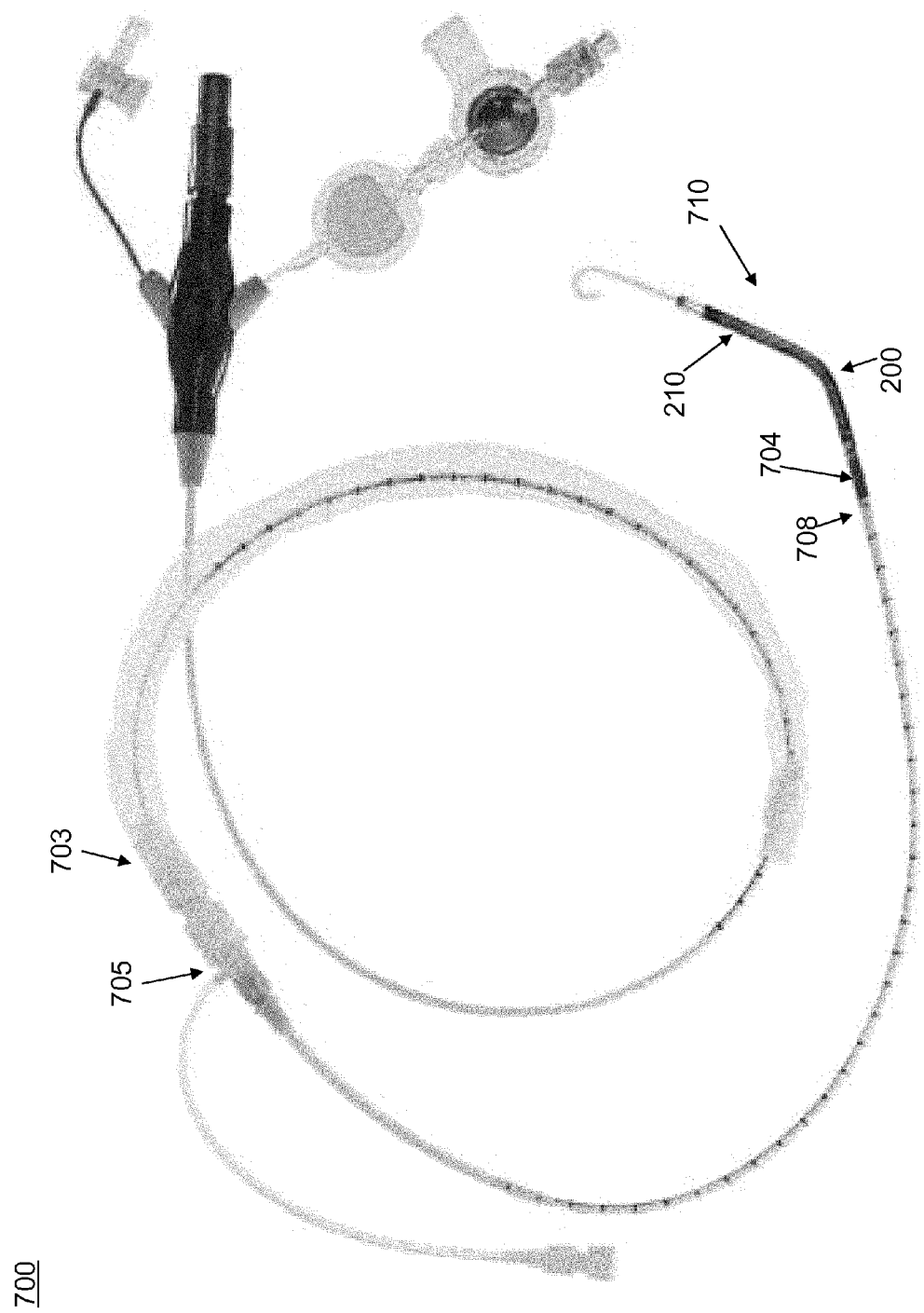
FIG. 7 is an illustration of an intracardiac blood pump system featuring a cannula with a radiopaque marker.

FIG. 7 shows a catheter system 700 with an intracardiac blood pump 701. The pump 701 includes a cannula with a radiopaque markers of the type described herein. The pump 701 may be, for example the Impella 2.5 blood pump available from Abiomed Inc. of Danvers, Mass., modified to include the cannula 200 having a radiopaque marker 210 as described herein. The blood pump 701 is a catheter mounted microaxial flow pump capable of pumping up to, e.g., 2.5 L/min of blood from the left ventricle to the systemic circulation. Using a monorail type insertion platform, the blood pump 701 is placed via a femoral arterial sheath 703 (e.g., a 13 Fr sheath). The blood pump includes a cannula 200 featuring a radiopaque marker 210. The cannula portion of the device which, during use, sits across the aortic valve is contiguous to and integrated motor 704 that comprises the largest diameter section of the catheter (e.g., at 12 Fr). A repositioning device 705 allows removal of the sheath 703 after placement, leaving the modest (e.g. 9 F) catheter in the arterial system. The pump 701 is powered and controlled by a control console (not shown), e.g., an Impella series control panel available from Abiomed Inc. of Danvers, Mass. An arterial infusion pump (not shown) controls a purge system designed to keep the corrosive plasma from entering the motor compartment of the pump 701.

Figure 8:
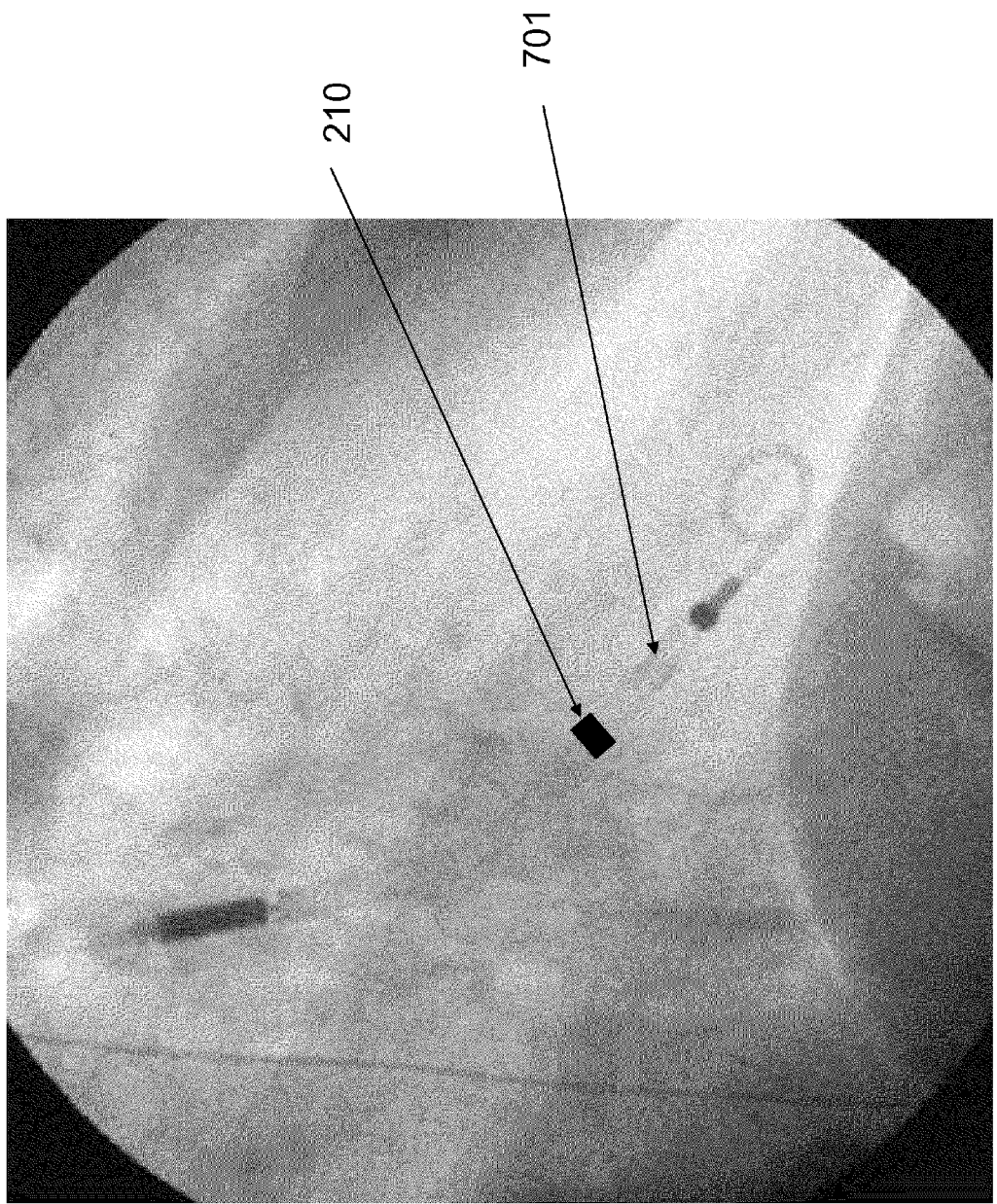
FIG. 8 is an illustration of a fluoroscopic image of an intracardiac blood pump featuring a cannula with a radiopaque marker being placed in a subject.

The pump 701 is inserted via a modified monorail technique under direct fluoroscopic control. pressure monitoring using a pressure lumen 708 adjacent to the motor as well as motor current monitoring are used to give positioning verification to the operator. The device is placed using fluoroscopic control to avoid kinking the catheter and compromising the purge lumen. After arterial access is obtained, the 13 F peel-away sheath is positioned. A coronary guiding catheter (e.g., a JR-4 cathether) and subsequently a 0.018" wire is placed across the aortic valve into the left ventricle. Once the 0.018" wire is across the aortic valve, the guiding catheter is removed and the pump catheter is threaded onto the 0.018" wire. With the device positioned in the ventricle (as shown in FIG. 8), the wire is removed and the pump 701 activated at minimum level, just enough to counteract the regurgitation coming down the cannula from the proximal aorta into the ventricle now that the cannula is placed across the aortic valve.

Once the pump 701 is positioned across the aortic valve, the control panel can be utilized to confirm that the device placement is proper and stable. At this point, the device performance level is typically adjusted to a higher performance level.

Throughout the procedure described above, the radiopaque marker 210 on the cannula 200 may be used to assist the practitioner in placement of the pump 701. For example, FIG. 8 shows an illustration of a fluoroscopic of the pump 701, during insertion. The radiopaque marker 801 is clearly visible.

Further details regarding the use of the system 700 may be found in D. H. Raess and D. M. Weber, J. of Cariovasc. Trans. Res. (2009) 2:168-172.

Although a number of examples have been given above related to the provision of radiopaque markers for a cannula used with intracardiac blood pumps, it is to be understood that the techniques applied herein may be used for other applications, including any suitable types of medical devices intended for use on human or animal subjects.

In various embodiments, the radiopaque markers described herein have sufficient radiopacity to be clearly visible under conventional fluoroscopic conditions.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one."

The phrase "or," as used herein in the specification and in the claims, should be understood to mean "either or both" of the elements so conjoined, i.e., elements that are conjunctively present in some cases and disjunctively present in other cases. Multiple elements listed with "or" should be construed in the same fashion, i.e., "one or more" of the elements so conjoined. Other elements may optionally be present other than the elements specifically identified by the "or" clause, whether related or unrelated to those elements specifically identified. Thus, as a non-limiting example, a reference to "A or B", when used in conjunction with open-ended language such as "including" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "or" as defined above. For example, when separating items in a list, "or" or "or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

In the claims, as well as in the specification above, all transitional phrases such as "including," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

All definitions, as defined and used herein, should be understood to control over dictionary definitions, definitions in documents incorporated by reference, and/or ordinary meanings of the defined terms.

Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A method of applying a radiopaque marker to a cannula for use with an intracardiac pump, the method comprising:
    obtaining a band of radiopaque polymer material;
    placing the band around an outer diameter of the cannula, the cannula comprising a flexible tubular wall formed around and supported by a coil of shape memory material;
    placing a heat shrink tube around the band and the cannula;
    heating the band and the polymer tube to:
        soften the band;
        cause the heat shrink tube to shrink and apply force on the softened band towards the cannula; and
        cause the softened band to be welded to the cannula to form a radiopaque marker in a portion of the tubular wall; and
    removing the heat shrink tube;
    wherein the radiopaque band comprises a mixture of a radiopaque material with a non-radiopaque polymer, and wherein the mixture includes at least 80% of the radiopaque material by weight.

2. The method of claim 1, wherein, after removing the heat shrink tube, the portion of the tubular wall comprising the radiopaque marker has a substantially smooth outer surface.

3. The method of claim 2, wherein the outer diameter of the portion of the tubular wall comprising the radiopaque marker varies from the outer diameter of an adjacent portion not comprising the radiopaque marker by less than 0.1%.

4. The method of claim 2, wherein the outer diameter of the portion of the tubular wall comprising the radiopaque marker varies from the outer diameter of an adjacent portion not comprising the radiopaque marker by less than 0.01%.

5. The method of claim 2, wherein the outer diameter of the portion of the tubular wall comprising the radiopaque marker is substantially the same as the outer diameter of an adjacent portion not comprising the radiopaque marker.

6. The method of claim 2, wherein the portion of the tubular wall comprising the radiopaque marker has a substantially smooth outer surface that is substantially free of surface variations that would promote haemolysis or thrombus during use.

7. The method of claim 2, further comprising forming the radiopaque band, wherein forming the radiopaque band comprises:
   mixing the radiopaque material with the non-radiopaque polymer to form the mixture;
   forming a radiopaque tube by extruding the mixture;
   cutting the radiopaque tube to form at least one band.

8. A method of applying a radiopaque marker to a cannula for use with an intracardiac pump, the method comprising:
   obtaining a radiopaque metallic element;
   placing a marker comprising the metallic element in contact with an outer diameter of the cannula, the cannula comprising a flexible tubular polymer wall supported by a coil of shape memory material;
   placing a sleeve of a non-metallic material surrounding the a radiopaque metallic element and the cannula;
   placing a heat shrink tube surrounding sleeve;
   heating the sleeve and the heat shrink tube
      soften the sleeve;
      cause the heat shrink tube to shrink and apply force on the softened band towards the cannula; and
      cause the softened band to be welded to the cannula around the element to form a radiopaque marker in a portion of the tubular wall; and
   removing the heat shrink tube.

9. The method of claim 8, wherein, after removing the heat shrink tube, the portion of the tubular wall comprising the radiopaque marker has a substantially smooth outer surface of non-metallic material which surrounds the element.

10. The method of claim 9, wherein the outer diameter of the portion of the tubular wall comprising the radiopaque marker varies from the outer diameter of an adjacent portion not comprising the radiopaque marker by less than 1.0%.

11. The method of claim 9, wherein the outer diameter of the portion of the tubular comprising the radiopaque marker varies from the outer diameter of an adjacent portion not comprising the radiopaque marker by less than 0.1%.

12. The method of claim 9, wherein the element is completely covered by the smooth outer layer, such that no surfaces or edges of the marker are exposed.

13. The method of claim 12, wherein the smooth outer layer is substantially free of variations in outside diameter corresponding to the covered marker.

14. The method of claim 12, wherein the smooth outer layer is substantially free of surface variations that would promote haemolysis or thrombus during use.

15. The method of claim 12, wherein:
   the element comprises an elastic member, and
   placing the element in contact with an outer diameter of the cannula comprises using an elastic force from the elastic member to clamp the element to the cannula.

16. The method of claim 15, wherein the element comprises a C-shaped partial ring.

17. The method of claim 15, wherein the smooth outer surface prevents the element from moving along a length of the cannula.

18. A cannula having a radiopaque marker for use with an intracardiac pump produced using the method of claim 1.

19. A cannula having a radiopaque marker for use with an intracardiac pump produced using the method of claim 8.

* * * * *